(12) United States Patent
Brunham (10) Patent No.: US 7,229,975 B1
(45) Date of Patent: Jun. 12, 2007

(54) **DNA IMMUNIZATION AGAINST *CHLAMYDIA* INFECTION**

(75) Inventor: Robert C. Brunham, Vancouver (CA)

(73) Assignee: University of Manitoba, Winnipeg, Manitoba (CA)

(*) Notice: Subject to any disclaimer, the term of this patent is extended or adjusted under 35 U.S.C. 154(b) by 427 days.

(21) Appl. No.: 10/088,569

(22) PCT Filed: Sep. 21, 2000

(86) PCT No.: PCT/CA00/01097

§ 371 (c)(1),
(2), (4) Date: Aug. 13, 2002

(87) PCT Pub. No.: WO01/21811

PCT Pub. Date: Mar. 29, 2001

Related U.S. Application Data (63) Continuation-in-part of application No. 09/401,780, filed on Sep. 12, 1999, now Pat. No. 6,632,663.

(51) Int. Cl.
- A61K 48/00 (2006.01)
- A61K 31/70 (2006.01)
- C07H 21/02 (2006.01)
- C07H 21/04 (2006.01)
- A01N 43/04 (2006.01)

(52) U.S. Cl. .................. 514/44; 536/23.1; 536/23.7
(58) Field of Classification Search ............... 514/44; 536/23.1, 23.7
See application file for complete search history.

(56) References Cited

U.S. PATENT DOCUMENTS

| | | | |
|---|---|---|---|
| 5,589,466 A | 12/1996 | Felgner et al. | ................ 514/44 |
| 6,001,372 A * | 12/1999 | DeMars et al. | .......... 424/263.1 |

FOREIGN PATENT DOCUMENTS

| | | |
|---|---|---|
| EP | 0192033 | 8/1986 |
| WO | WO 98/02546 A | 1/1998 |

OTHER PUBLICATIONS

Alberts et al. (1994, Molecular Biology of the Cell, Third Edition, Garland Publishing: New York, p. 1195).*
NCBI nucleotide printout, *Chlamydia trachomatis* D/UW-3/Cs section 15 of 87 of the complete genome, gi No.: 3328545.*
Read et al. 2000, Nucleic Acid Research 28: 1397-1406.*
Stephens RS et al. 1998, Science, 282: 754-759.*
Chattergoon et al. 1997, The FASEB Journal, 11: 753-763.*
Ulmer, 2001, Curr. Opin. Drug Discov. Devel. 4: 192-7. see abstract.*
Cui, 2005, Adv. Genet. 54: 257-289, see abstract.*
Proceedings of the Chlamydia Vaccine Development Colloquium, Jun. 4-5, 2003, edited by Woodall, J.P., The Albert B. Savin Vaccine Institute, 1st edition.*
Somia and Verma, 2000, Nature Reviews: Genetics, 1: 91-99.*
Minchin et al., 2001, J. of Pharm. and Exp. Therap., 296: 1006-1012.*
Donnelly et al, Protective efficacy of intramuscular immunization with naked DNA. vol. 772 40-46 (1995).
D. M. Pardoll and A. M. Beckerieg, Exposing the immunology of naked DNA vaccines. vol. 3, 165-169 (1995).
W.M. McDonnell and F. K. Askari, Molecular Medicine. DNA vaccines. vol. 334, 42-45 (1996).
J. B. Ulmer et al., Heterologous protection against influenza by injection of DNA encoding a viral protein. vol. 259, 1745-1749 (1993).
B. Wang et al., Gene inoculation generates immune responses against human immunodeficiency virus type 1. vol. 90, 4156-4160 (1993).
G. J. M. Cox, et al., Bovine Herpesvirus 1: Immune responses in mice and cattle injected with plasmid DNA. vol. 67, 5664-5667 (1993).
E. Raz et al., Intradermal gene immunization: the possible role of DNA uptake in the induction of cellular immunity to viruses. vol. 91, 9519-9523 (1994).
Z. Q. Xiang et al., Vaccination with a plasmid vector carrying the rabies virus glycoprotein gene induces protective immunity against rabies virus. 199, 132-140 (1994).
J.J. Donnelly et al., Protection against papillomavirus with a polynucleotide vaccine. vol. 713, 314-320 (1996).
D. L. Montgomery et al., Heterologous and homologous protection against influenza A by DNA vaccination: Optimization of DNA vectors. vol. 12, 777-783 (1993).
J.J. Donnelly et al., Preclinical efficacy of a prototype DNA vaccine: Enhanced protection against antigenic drift in influenza virus. vol. 1, 583-587 (1995).
G. H. Rhodes et al., Characterization of humoral immunity after DNA injection. vol. 82, 229-236 (1994).
H. L. Davis, M. L. Michel, R. G. Whalen, DNA-based immunization induces continuous secretion of hepatitis B surface antigen and high levels of circulating antibody. vol. 2, 1847-1851 (1993).
J. B. Ulmer. Protective immunity by intramuscular injection of low doses of influenza virus DNA vaccines. vol. 12, 154 1-1544 (1994).

(Continued)

*Primary Examiner*—Anne M. Wehbe'
*Assistant Examiner*—Joanne Hama
(74) *Attorney, Agent, or Firm*—Sim & McBurney; Michael I. Stewart (57) ABSTRACT

Nucleic acid, including DNA, immunization is used to generate a protective immune response in a host, including humans, to a serine-threonine kinase (STK) of a strain of *Chlamydia*. A non-replicating vector, including a plasmid vector, contains a nucleotide sequence encoding a STK or a fragment of the STK that generates antibodies that specifically react with STK and a promoter sequence operatively coupled to the first nucleotide sequence for expression of the STK in the host. The non-replicating vector may be formulated with a pharmaceutically-acceptable carrier for in vivo administration to the host.

3 Claims, 4 Drawing Sheets

OTHER PUBLICATIONS

Z. Xiang and H. C. J. Ertl. Manipulation of the immune response to a plasmid-encoded viral antigen by coinculation with plasmids expressing cytokines. vol. 2, 129-135 (1995).

E. F. Fynan et al, DNA vaccines: Protective immunization by parenteral, mucosal, and gene-gun inoculations, vol. 90, pp. 11478-11482 (1993).

E. Manickan, et al., Genetic immunization against herpes simplex virus. vol. 155, 259-265 (1995).

M. Sedegah et al , Protection against malaria by immunization with plasmid DNA encoding circumsporozoite protein. vol. 91, pp. 9866-9870 (1994).

M.A. Barry, et al., Protection against mycoplasma infection using expression-library immunization. vol. 377, 632-635 (1995).

D. Xu and F. Y. Liew, Genetic vaccination against leishmaniasis. vol. 12, 1534-1536 (1994).

D. B. Lowrie, et al., Towards and DNA vaccine against tuberculosis. vol. 12, 1537-1540 (1994).

J. W. Moulder, et al., Interaction of chlamydiae and host cells in vitro. vol. 55, 143-190 (1991).

J. Schachter, The intracellular life of chlamydia. vol. 138, 109-139 (1988).

S. D. Hillis and J. N. Wasserheit, Screening for chlamydia-a key to the prevention of pelvic inflammatory disease. vol. 334, 1399-1401 (1996).

R. C. Brunham and R. W. Peeling, *Chlamydia trachomatis* antigens: Role in immunity and pathogenesis. vol. 3, 218-233 (1994).

R. P. Morrison, D.S. Manning, H. D. Caldwell, Immunology of *chlamydial trachomatis* infections. 1992, pp. 57-84.

J. T. Grayston and S-P. Wang, The potential for vaccine against infection of the genital tract with *chlamydia trachomatis*. vol. 5, 73-77 (1978).

J. T. Grayston and S.-P Wang, New knowledge of chlamydia and the diseases they cause. vol. 132, 87-105 (1975).

H. R. Taylor, et al. Oral immunization with chalmydia major route membrane protein (MOMP) vol. 29, 1847-1853 (1988).

B.E. Batteiger, et al., Partial protection against genital reinfection by imunization of guinea pigs with isolated outer-membrane proteins of the chlamydial agent of guinea-pig inclusion conjuctivitis. 139, pp. 2965-2972 (1993).

M. Campos et al., A chlamydial major outer membrane protein extract as trachoma vaccine candidate. vol. 36, 1477-1491 (1995).

H. Su, M. Parnell, et al., Protective efficacy of parenterally administered MOMP-derived synthetic oligopeptide vaccine in a murine model of *Chlamydia trachomatis* gential tract infection: serum neutralizing IgG antibodies do not protect against chlamydial genital tract infection. vol. 13, 1023-1032 (1995).

T.-W. Tan, Protection of sheep against *chlamudia psittaci* infection with a subcellular vaccine containing the major outer membrane protein. vol. 58, 3101-3108 (1990).

M. Tuffrey, et al., Heterotypic protection of mice against chlamydial salpingitis and colonization of the lower genital tract with a human serovar F isolate of *Chlamudia trachomatis* by prior immunization with recombinant serovar L1 major outer-membrane protein. 138, 1707-1715 (1992).

Y.-X. Zhang, J. G. Fox, Y. Ho., Comparsion of the major Outer-Membrane protein (MOMP) gene of mouse pneumonitis (MoPn) and hamster SFPD strans of *chlamydia trachomatis* with other Chlamydia strains. 10(6), pp. 1327-1342 (1993).

R. P. Morrison, et al., Gene knockout mice establish a primary protective role for major histocompatibility complex class II-Restricted responses in *chlamydia trachomatis* genital tract infection, vol. 63, 4661-4668 (1995).

H. Su and H. D. Caldwell, CD4$^+$ T cell play a singnificant role in aadoptive immunity to *chlamydia trachomatis* infection of the mouse genital tract. vol. 63, 3302-3308 (1995).

J. U. Igietseme et al., Resolution of murine chlamydial genital infection by the adoptive transfer of Biovar-Specific, TH1 Lymphocyte Clone. 5, 317-324 (1993).

J. U. Igietseme, et al., Susceptibility to reinfection after a primary chlamydia genital infection is associated with a decrease of antigen-specific T cells in the genital tract. vol. 59, 1346-1351 (1991).

D. M. Williams, et al., Cellular immunity to the mouse pneumonitis agent. vol. 149, 630-639 (1984).

G. Tipples and G. McClarty, Cloning and expression of the *chlamydia trachomatis* gene for CTP synthetase. vol. 270, 7908-7914 (1995).

X. Yang, K. et al., Genetically determined differences in IL-10 and IFN-v response correlate with clearance of chlanydia trachomatid mouse pneumonitis inflection. vol. 156, 4338-4344 (1996).

Tang et al., Genetic immunization is a simple method for eliciting an immune response. 1992, vol. 356, pp. 152-154.

Davis et al., Direct gene transfer in skeletal muscle: plasmid DNA-based immunization against the hepatitis B virus surface antigen. 1994, vol. 12: 1503-1509.

Holzman L.B. et al., Identification, molecualr cloning, and characterzation of dula leucine zipper bearing kinase. 1994. pp. 30808-30817, XP-002120730.

Stephens, R.S. et al., Genome sequence of an obligate intracellular pathogen of humnas: *Chlamydia trachomatis*. vol. 282 (1998) pp. 759-759 XP-002104802.

Green et al, "Liposomal Vaccines", Adv. Exp. Med. Biol. 383:83-92.

Baxby et al, "Potential use of nonreplicating vectors as recombinant vaccines", Vaccine, 10(1):8-9.

Anderson et al, Immune response in mice following immunization with DNA encoding fragment C of tetanus toxin, Inf. Immun. 64(8): 3168-3173.

Kaul et al, "Expression of the *Chlamydia trachomatis* major outer membrane protein-encoding gene in *Escherichia coli*: role of the 3' end in mRNA stability," Gene 87(1):97-104.

Douglas et al, "Mutagenesis of the P2 promoter of the major outer membrane protein gene of *Chlamydia trachomatis*", J. Bacteriol., 178(19):5573-5578.

Dascher et al, "Expression and translocation of the chlamydial major outer membrane protein in *Escherichia coli*", Microbial Pathogenesis, 15: 455-467.

M.A. Liu, M.R. Hilleman, R.Kurth, Overview of DNA Vaccines Ann. N.Y. Acad. Sci. 772 (1995) pp. 15-20.

* cited by examiner

FIG. 1A

* p<0.05, **p<0.01, when compared with pcDNA3 group

*Chlamydia trachomatis* Serine threonine k

FIG.3B

```
946   TTC TGT TAT GCT CAG GGG CAC TGT AGT TTT GCT CTT AGT ATG ATC  990
991   AAA CAG TTT CTT AAT CAG GAG AAA GCG CAA GCG CAT ATC CCA      1035
1036  ACA GTA ATA AAA ACA GGA CAG ACA CTT TGT AAA ACA CAT ATT      1080
1081  CCG CTT TGT GAA ACT TTG GAT ACT TCC TGC ATG TTT ATA CAT TTC  1125
1126  CAA CAA GAA CTC ATG GGG TGT TGC TGT GGG AAA ACT GAT TTC TTC  1170
1171  TTA AAA AAG CAA ACG AGG GGA GTG CAA CGT TTT CAA GCG GAA TCG  1215
1216  CAA GGA ATA GGG GAG GGA CCC CTG AIC CAC AAA CAA TCT          1260
1261  TTT TTG TGG GAA CCT GGT GAT GAG CTT ATC GTA CAC ACC CCG AGG  1305
1306  GCT AGA GAT TTG GTA TAT TTA TAC TGT CCT TCT CTG AAG TTG      1350
1351  CAA GAT AGA GGG CAA ATG GAT TTC TGC CAA ACA GAT TAC CTT      1395
1396  CAG AAG GAA GTG AGG CAG TAT GAC AAG GGA AGT CCT TAT TCA      1440
1441  ACA CTT ATC AGC TTA AAA AGA GTC CGG                          1467
```

SEQUENCE LISTING

<160> NUMBER OF SEQ ID NOS: 3

<210> SEQ ID NO 1
<211> LENGTH: 1467
<212> TYPE: DNA
<213> ORGANISM: Chlamydia trachomatis

<400> SEQUENCE: 1

```
atgcttgaat taggcgtatc gtttccttcc aagactaaat atcttctgac acgagaactt      60
agtcgtaagg taggcttgac tgtctatcaa ggagtggatg agagttcttc tcgtcctgtg     120
gtgatcaaag cattggtatc tccagggatt catgaccagc gttttcttcg tgcttttgaa     180
gaagaagcta ggattatgca acttgtagat catccggcat ttgttcgatt agaagaaaaa     240
ggtgagtggg agcaaggacg ttatttcgtt tctgaatata ttttagggca ttcattgcga     300
gatattatcc tttcatctca tctcgctttg gataaggcag tttctattgt tttacaagta     360
gcgcaggcaa taacggctct tcataaacat catgttttac atctcgatat taaacctgaa     420
aacatcatga tttctcggtt gggagaggtc aagttgatcg attatgggct ttcagcctgg     480
caatttaatc attggggttc gcctgcatat atgagtcccg aacagagcag gcaggaaaag     540
ctatctcccg catccgatgt gtatgcttta gctttgttag cttatgagct gattatgggg     600
cagctttctt taggaaaggt ctatttatct ttactccccg taaagattag taaagtgtta     660
actcaagcat tgcaaccaga cccagaagca cggtttcctt ctatgcaaga gtttgctacg     720
gctttgcaag attatcttat gcatgatgtg cacgaagatt atcgtaaaaa agatcgcgta     780
atcatgcagt ttgaacagtt gcagcaacaa aatatgtggc tggctccaga taagctttgc     840
atgccggaag ggatggctct gcacatttat tcacaaaaag agccctgtga tttacataat     900
gtttactatg atatacttag gtctgaggat atagtagaat tgtggttctg ttatgctcag     960
gggcactgta gttttgctct tagtatgatc aaacagtttc ttaatcagcg aacagagaaa    1020
```

-continued

```
gcgcaagata tcccaacagt aataaaaaca ttggatactc tttgtaaaac aatgcatatt    1080
ccgctttgtg aaaagggat ttcctgctgc tgttttatat ttttccaaca agaactcatg     1140
tgcttttctt gtgggaaaac tgatttctcg ttaaaaaagc aaacgagggg agtgcaacgt    1200
tttcaagcgg aatcgcaagg aatagggaa gagggacccc tggagatcca caaacaatct    1260
tttttgtggg aacctggtga tgagcttatc gtacacaccc cgagggctag agatttggta    1320
tatttatact gtccttcttt cctgaagttg caagatagag ggcaaatgga tatattctgc    1380
caaacagatt accttcagaa ggaagtgagg cagaagtatg acggaagtct ttatccttca    1440
acacttatca gcttaaaaag agtccgg                                        1467
```

<210> SEQ ID NO 2
<211> LENGTH: 41
<212> TYPE: DNA
<213> ORGANISM: Chlamydia trachomatis

<400> SEQUENCE: 2

```
ggggatccgc caccatgctt gaattaggcg tatcgtttcc t                        41
```

<210> SEQ ID NO 3
<211> LENGTH: 40
<212> TYPE: DNA
<213> ORGANISM: Chlamydia trachomatis

<400> SEQUENCE: 3

```
ggggctcgag ctattaccgg actcttttta agctgataag                          40
```

US 7,229,975 B1

DNA IMMUNIZATION AGAINST *CHLAMYDIA* INFECTION

REFERENCE TO RELATED APPLICATIONS

This application is a United States National Phase application filing under 35 USC 371 of PCT/CA00/01097 filed Sep. 21, 2000, which is a continuation-in-part of U.S. patent application Ser. No. 09/401,780 filed Sep. 12, 1999 (Now U.S. Pat. No. 6,632,663).

FIELD OF INVENTION

The present invention relates to immunology and, in particular, to immunization of hosts using nucleic acid to provide protection against infection by *Chlamydia*.

BACKGROUND OF THE INVENTION

DNA immunization is an approach for generating protective immunity against infectious diseases (ref 1—throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). Unlike protein or peptide based subunit vaccines, DNA immunization provides protective immunity through expression of foreign proteins by host cells, thus allowing the presentation of antigen to the immune system in a manner more analogous to that which occurs during infection with viruses or intracellular pathogens (ref 2). Although considerable interest has been generated by this technique, successful immunity has been most consistently induced by DNA immunization for viral diseases (ref. 3). Results have been more variable with non-viral pathogens which may reflect differences in the nature of the pathogens, in the immunizing antigens chosen, and in the routes of immunization (ref. 4). Further development of DNA vaccination will depend on elucidating the underlying immunological mechanisms and broadening its application to other infectious diseases for which existing strategies of vaccine development have failed.

*Chlamydia trachomatis* is an obligate intracellular bacterial pathogen which usually remains localized to mucosal epithelial surfaces of the human host. Chlamydiae are dimorphic bacteria with an extracellular spore-like transmission cell termed the elementary body (EB) and an intracellular replicative cell termed the reticulate body (ref. 5). From a public health perspective, chlamydial infections are of great importance because they are significant causes of infertility, blindness and are a prevalent co-factor facilitating the transmission of human immunodeficiency virus type 1 (ref. 6). Protective immunity to *C. trachomatis* is effected through cytokines released by Th1-like CD 4 lymphocyte responses and by local antibody in mucosal secretions and is believed to be primarily directed to the major outer membrane protein (MOMP), which is quantitatively the dominant surface protein on the chlamydial bacterial cell and has a molecular mass of about 40 kDa (ref. 16).

Initial efforts in developing a chlamydial vaccine were based on parenteral immunization with the whole bacterial cell. Although this approach met with success in human trials, it was limited because protection was short-lived, partial and vaccination may exacerbate disease during subsequent infection episodes possibly due to pathological reactions to certain chlamydial antigens (ref. 8). More recent attempts at chlamydial vaccine design have been based on a subunit design using MOMP protein or peptides. These subunit vaccines have also generally failed, perhaps because the immunogens do not induce protective cellular and humoral immune responses recalled by native epitopes on the organism (ref. 9).

In copending U.S. patent application Ser. No. 08/893,381 filed Jul. 11, 1997, assigned to University of Manitoba and the disclosure of which is incorporated herein by reference (WO 98/02546), I have described the generation of a protective immune response using a DNA sequence which encodes the MOMP of *C. trachomatis* in a plasmid by DNA immunization.

SUMMARY OF THE INVENTION

The present invention is concerned with nucleic acid immunization, specifically DNA immunization, to generate in a host protective antibodies to a serine-threonine kinase of a strain of *Chlamydia*. DNA immunization induces a broad spectrum of immune responses including Th1-like CD4 responses and mucosal immunity.

Accordingly, in one aspect, the present invention provides a non-replicating vector comprising a nucleotide sequence encoding a serine-threonine kinase (STK) or a fragment of STK that generates a STK-specific immune response, and a promoter sequence operatively coupled to said nucleotide sequence for expression of said STK in a host to which the vector is administered.

The promoter may be a cytomegalovirus promoter, and may be contained in the human cytomegalovirus major immediate-early promoter-enhancer region. The vector may be a plasmid vector and the nucleotide sequence may be that of SEQ ID No: 1.

The strain of *Chlamydia* may be a strain of *Chlamydia* inducing chlamydial infection of the lung, including *Chlamydia trachomatis* or *Chlamydia pneumoniae*. The non-replicating vector may be plasmid pcDNA3 into which the nucleotide sequence is inserted. The pcDNA3 vector may contain the nucleotide sequence having SEQ ID No: 1.

In a further aspect of the present invention, there is provided an immunogenic composition for in vivo administration to a host for the generation in the host of a protective immune response to a serine-threonine kinase (STK) of a strain of *Chlamydia*, comprising a non-replicating vector as provided herein and a pharmaceutically-acceptable carrier therefor.

In an additional aspect of the invention, there is provided a method of immunizing a host against disease caused by infection with a strain of *Chlamydia*, which comprises administering to said host an effective amount of a non-replicating vector as provided herein.

In these aspects of the present invention, the various options and alternatives discussed above for the non-replicating vector may be employed.

The non-replicating vector may be administered to the host, including a human host, in any convenient manner, such as intramuscularly or intranasally.

The present invention also includes, in a further aspect thereof, a method of using a gene encoding a serine-threonine kinase (STK) of a strain of *Chlamydia* or a fragment of said STK that generates a STK-specific immune response, to produce an immune response in a host, which comprises isolating said gene; operatively linking said gene to at least one control sequence to produce a non-replicating vector, said control sequence directing expression of said STK or fragment thereof when introduced into a host to produce an immune response to said STK or fragment thereof; and introducing said vector into a host.

In an additional aspect of the invention, there is provided a method of producing a vaccine for protection of a host against disease caused by infection with a strain of *Chlamydia*, which comprises isolating a nucleotide sequence encoding a serine-threonine kinase (STK) of a strain of *Chlamydia* or a fragment of the STK that generates a STK-specific immune response, operatively linking said nucleotide sequence to at least one control sequence to produce a non-replicating vector, the control sequence directing expression of said STK or fragment thereof when introduced to a host to produce an immune response to said STK or fragment thereof, and formulating said vector as a vaccine for in vivo administration to a host.

The various options and alternatives discussed above may be employed in this aspect of the invention.

Advantages of the present invention, therefore, include a method of obtaining a protective immune response to infection carried by a strain of *Chlamydia* by DNA immunization of DNA encoding the major outer membrane protein of a strain of *Chlamydia*.

BRIEF DESCRIPTION OF DRAWINGS

FIG. 1A: body weight of the mice was measured daily after challenge infection until mice were sacrificed at day 10. FIG. 1B: mice were sacrificed at postinfection day 10, and MoPn growth in lung was analyzed by quantitative tissue culture. Data are mean±SE of $\log_{10}$ IFU/lung. *$p<0.05$, $p<0.01$ vs. pcDNA-treated group. Legend: EB=host-killed elementary bodies, STK=plasmid DNA, N=native, pcDNA3=empty vector.

GENERAL DESCRIPTION OF THE INVENTION

To illustrate the present invention, plasmid DNA was constructed containing the serine-threonine kinase (STK) gene from the *C. trachomatis* mouse pneumonitis strain (MoPn), which is a natural murine pathogen, permitting experimentation to be effected in mice. It is known that primary infection in the mouse model induces strong protective immunity to reinfection. For human immunization, a human pathogen strain is used.

Any convenient plasmid vector may be used, such as pcDNA3, a eukaryotic II-selectable expression vector (Invitrogen, San Diego, Calif., USA), containing a human cytomegalovirus major-immediate-early promoter-enhancer region. The STK gene may be inserted in the vector in any convenient manner. The gene may be amplified from *Chlamydia* trachomatic genomic DNA by PCR using suitable primers and the PCR product cloned into the vector. The STK gene-carrying plasmid may be transferred, such as by electroporation, into *E. coli* for replication therein. Plasmids may be extracted from the *E. coli* in any convenient manner.

The plasmid containing the STK gene may be administered in any convenient manner to the host, such as intramuscularly or intranasally, in conjunction with a pharmaceutically-acceptable carrier.

The data presented herein and described in detail below demonstrates that DNA immunization with the *C. trachomatis* STK gene elicits immune responses and produces significant protective immunity to lung challenge infection with *C. trachomatis* MoPn.

It is clearly apparent to one skilled in the art, that the various embodiments of the present invention have many applications in the fields of vaccination, diagnosis and treatment of chlamydial infections. A further non-limiting discussion of such uses is further presented below.

1. Vaccine Preparation and Use

Immunogenic compositions, suitable to be used as vaccines, may be prepared from the STK genes and vectors as disclosed herein. The vaccine elicits an immune response in a subject which includes the production of anti-STK antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640) or the nucleic acid may be associated with an adjuvant, as described in more detail below. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly(8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The STK gene containing non-replicating vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the STK and antibodies thereto, and if needed, to produce a cell-mediated immune response. Precise amounts of active ingredient required to be administered depend on the judgement of the practitioner. However, suitable dosage ranges are readily determinable by one skilled in the art and may be of the order of about 1 g to about 1 mg of the STK gene-containing vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the non-replicating vector comprising a first nucleotide sequence encoding a STK gene of *Chlamydia* may be delivered in conjunction with a targeting molecule to target the vector to selected cells including cells of the immune system.

The non-replicating vector may be delivered to the host by a variety of procedures, for example, Tang et al. (ref 14) disclosed that introduction of gold microprojectiles coated with DNA encoding bovine growth hormone (BGH) into the skin of mice resulted in production of anti-BGH antibodies in the mice, while Furth et al. (ref. 15) showed that a jet injector could be used to transfect skin, muscle, fat and mammary tissues of living animals.

2. Immunoassays

The STK genes and vectors of the present invention are useful as immunogens for the generation of anti-STK antibodies for use in immunoassays, including enzyme-linked immunosorbent assays (ELISA), RIAs and other non-enzyme linked antibody binding assays or procedures known in the art. In ELISA assays, the non-replicating vector first is administered to a host to generate antibodies specific to the STK. These STK specific antibodies are immobilized onto a selected surface, for example, a surface capable of binding the antibodies, such as the wells of a polystyrene microtiter plate. After washing to remove incompletely adsorbed antibodies, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20 to 37 C. Following incubation, the sample-contacted surface is washed to remove non-immunocomplexed material. The washing procedure may include washing with a solution, such as PBS/Tween or a borate buffer. Following formation of specific immunocomplexes between the test sample and the bound STK specific antibodies, and subsequent washing, the occurrence, and even amount, of immunocomplex formation may be determined.

EXAMPLES

The above disclosure generally describes the present invention. A more complete understanding can be obtained by reference to the following specific Examples. These Examples are described solely for purposes of illustration and are not intended to limit the scope of the invention.

Changes in form and substitution of equivalents are contemplated as circumstances may suggest or render expedient. Although specific terms have been employed herein, such terms are intended in a descriptive sense and not for purposes of limitation.

Example 1

This Example shows the preparation of a plasmid vector for immunization.

The *C. trachomatis* mouse pneumonitis (MoPn) isolate was grown in HeLa 229 cells in Eagle MEM containing 10% fetal bovine serum and 2 mM L-glutamine. The MoPn EBs were harvested and purified by step gradient density centrifugation at 43,000 g for 60 min at 4° C. The purified EBs were washed twice with PBS, centifugated at 30,000 g for 30 min, resuspended in sucrose-phosphate-glutamic acid (SPG) buffer and frozen at −70° C. until used.

Figure 3B:
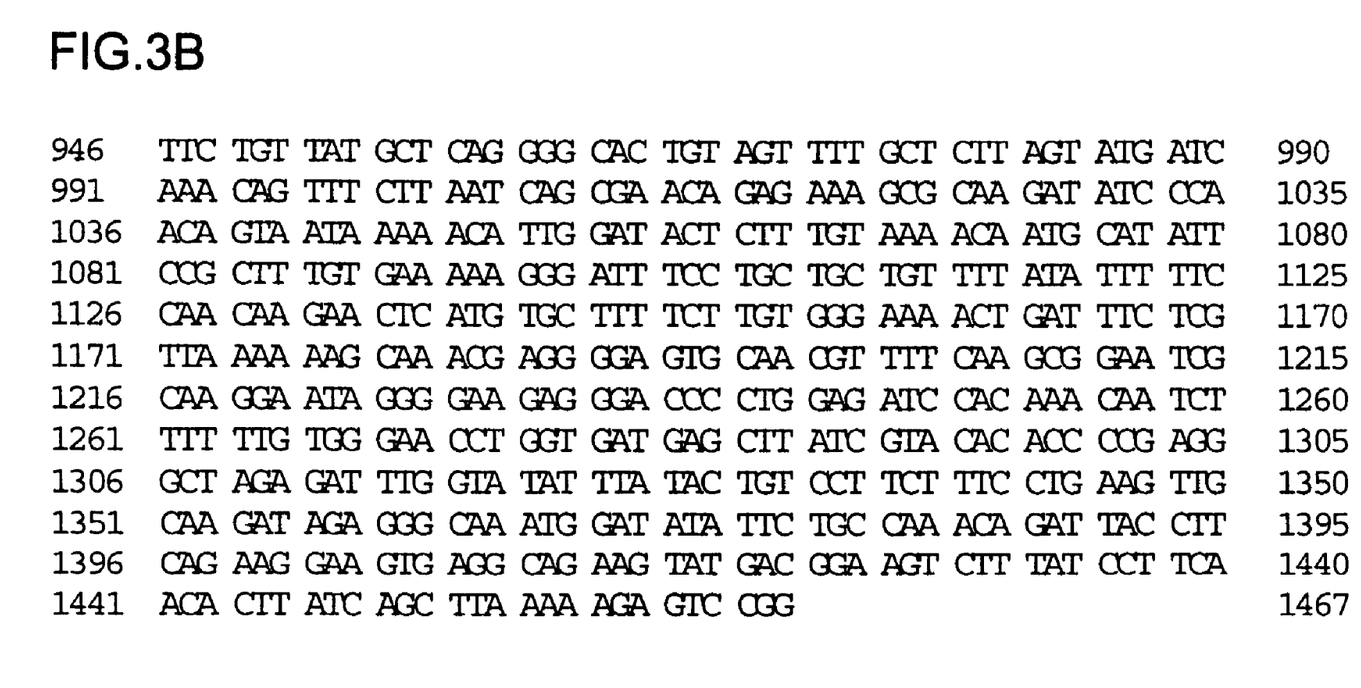
FIG. 3 shows the nucleic acid sequence of the STK gene (SEQ ID No: 1).

The serine-threonine kinase (STK) gene was cloned into eukaryotic expression plasmid, pcDNA3 (Invitrogen, San Diego) to form plasmid pcDNA3/STK. The STK gene was amplified from MoPn genomic DNA by polymerase chain reaction (PCR) with a 5' primer (GGG GAT CCG CCA CCA TGC TTG AAT TAG GCG TAT CGT TTC CT—SEQ ID No: 2) which included a BamHI site, a start codon, and the N-terminal sequence of the mature serine-threonine kinase of MoPn and a 3' primer (GGG GCT CGA GCT ATT ACC GGA CTC TTT TTA AGC TGA TAA G—SEQ ID No: 3) which include a XhoI site, two stop codons (CTA TTA), and the C-terminal sequence of the MoPn STK gene. After digestion with BamHI and XhoI, the PCR product, having the sequence shown in FIG. 3 (SEQ ID No: 1), was cloned into BamHI and XhoI restricted pcDNA3 with transcription under the control of human cytomegalovirus major intermediate-early promoter-enhancer region. The STK gene-encoding plasmid was transferred by electroporation into *Escherichia coli* DH5$_\alpha$, which was grown in Luria-Bertani (LB) broth containing 100 µg/ml ampicillin. The plasmid was extracted by a DNA purification system (Wizard Plus Maxiprep; Promega, Madison, Wis.), and the sequence of recombinant STK DNA was verified by PCR direct sequence analysis. Purified plasmid DNA was dissolved in saline at a concentration of 1 mg/ml. The DNA concentration was determined by spectrophotometry (DU-62; Beckman, Fullerton, Calif.) at 260 nm, and the size of the plasmid was compared with DNA standards in a ethidium bromide-stained agarose gel.

Example 2

This Example shows the results of immunizing studies using the plasmid vector.

Female Balb/c mice (4 to 5 weeks old) were purchased from Charles River Canada (St. Constant, Canada) mice were intramuscularly and intranasally immunized with plasmid DNA, prepared as described in Example 1, on three occasions, at 0, 2 and 4 weeks. For each immunization, a total of 200 µg DNA in 200 µl was injected into the two quadriceps muscles (100 µg of DNA/injection site) using a 27-gauge needle. At the same time, 50 µg DNA in 50 µl was delivered onto the nostrils of mice with a micropipette. The droplet was subsequently inhaled by the mice.

Mice were challenged intranasally with 2×10$^3$ IFU of *C. trachomatis* MoPn EB 14 days after last immunization, as described. Briefly, after ether anesthesia 25 µl of SPG containing an inoculum of 2×10$^3$ IFU of MoPn was delivered onto the nostrils of mice with a micropipette. The droplet was subsequently inhalted by the mice. Body weight was measured daily for 10 days following the challenge infection as a measure of chlamydia-induced morbidity. On postinfection day 10, the mice were sacrificed and their lungs were aseptically isolated and homogenized with grinder in SPG buffer. The tissue suspensions were centrifuged at 500 g for 10 min at 4° C. remove coarse tissue and debris. Supernatants were frozen at −70° C. until tissue culture testing for quantitative growth of the organism.

Figure 1A:
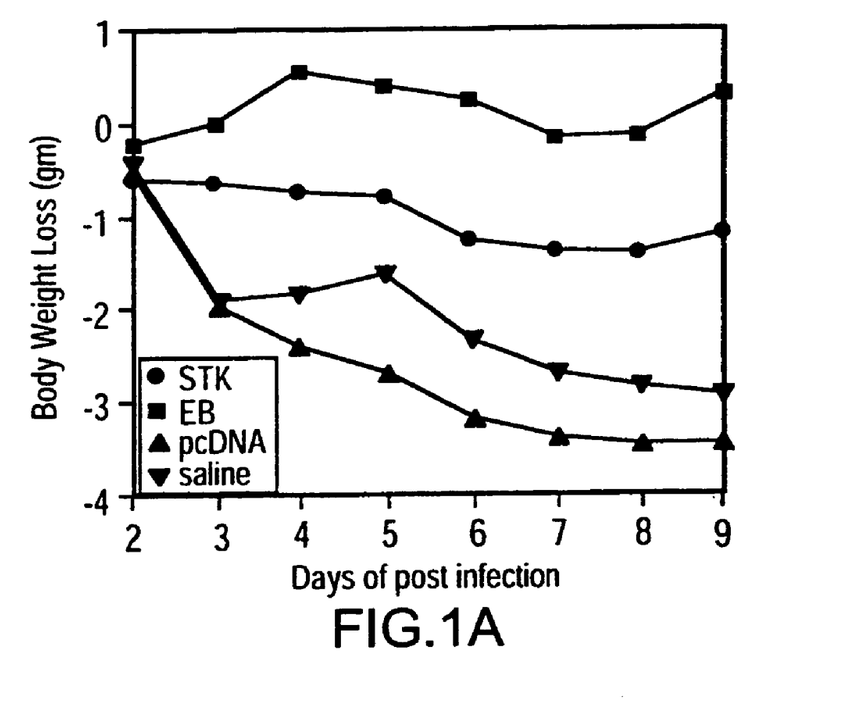
FIG. 1A and FIG. 1B show the results of immunization with serine-threonine kinase gene (pSTK) resulting in enhanced clearance of mouse pneumonitis (MoPn) infection in lung. Groups Balb/c mice were immunized with pSTK (n=5), pcDNA3 (n=6), saline (n=5) or with 1000 IFU of live MoPn EB (n=6). Fourteen days after last immunization, mice were challenged intranasally with infectious MoPn (2000 IFU).
Figure 1B:
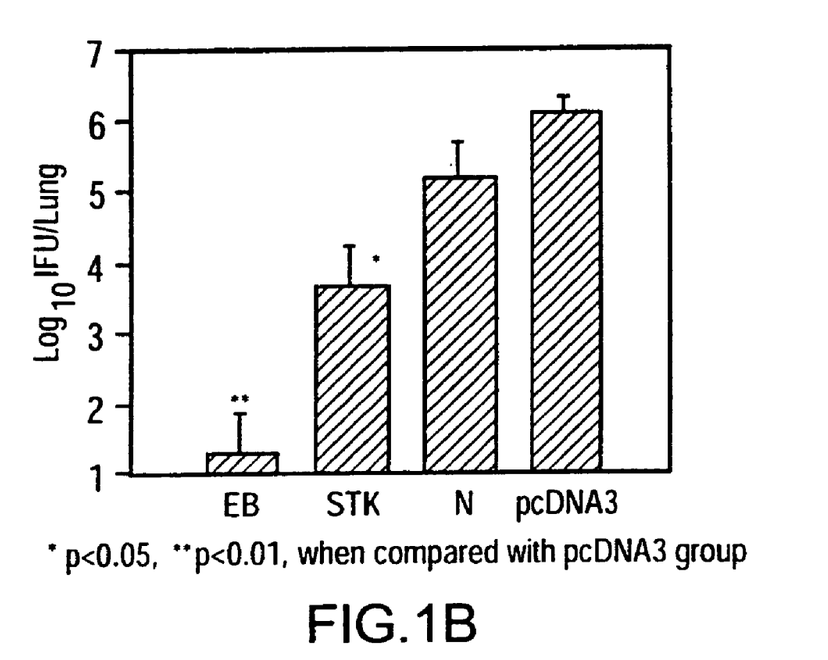
Figure 2:
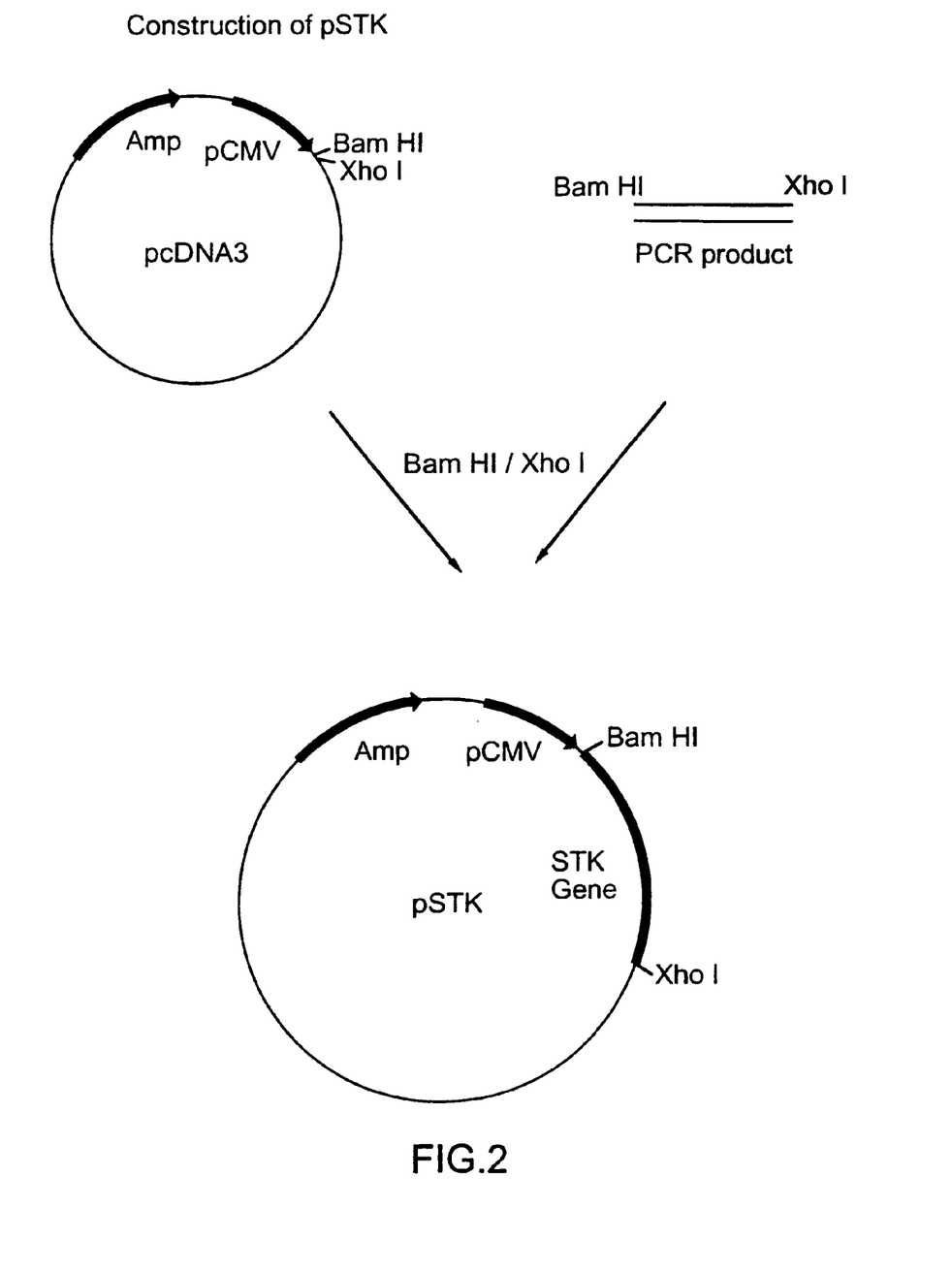
FIG. 2 shows the construction of plasmid pcDNA3/STK.

For more direct measure of the effectiveness of the DNA vaccination, the ability to limit the in vivo growth of *Chlamydia* following a sublethal lung infection was evaluated. In this infection model system, postchallenge day 10 is the time of peak growth and was chosen for comparison of lung titers among the various groups of mice. Mice immunized with STK DNA had a lung titer (log$_{10}$ IFU) is 31.6 and 316.2 folds lower than negative control groups (blank vector and saline groups).

SUMMARY OF DISCLOSURE

In summary of this disclosure, the present invention provides a method of nucleic acid, including DNA, immunization of a host, including humans, against disease caused by infection by strain of *Chlamydia*, specifically *C. trachomatis*, employing a non-replicating vector, specifically a plasmid vector, containing a nucleotide sequence encoding a serine-threonine kinase (STK) of a strain of *Chlamydia* and a promoter to effect expression of STK in the host. Modifications are possible within the scope of this invention.

REFERENCES

1. M. A. Liu, M. R. Hilleman, R. Kurth, Ann. N.Y. Acad. Sci. 772 (1995).
2. D. M. Pardoll and A. M. Beckerieg, Immunity 3, 165 (1995).
3. W. M. McDonnell and F. K. Askari, N. Engl. J. Med. 334, 42 (1996).
4. J. B. Ulmer et al., Science 259, 1745 (1993).
5. B. Wang et al., Proc. Natl. Acad. Sci. USA 90, 4156 (1993).
6. G. J. M. Cox, T. J. Zamb, L. A. Babiuk, J. Virol. 67, 5664 (1993).
7. E. Raz et al., Proc. Natl. Acad. Sci. USA, 91, 9519 (1994).
8. Z. Q. Xiang et al., Virology 199, 132 (1994).
9. J. J. Donnelly et al., J. Infect. Dis. 713, 314 (1996).
10. D. L. Montgomery et al., DNA. Cell. Biol. 12, 777 (1993).
11. J. J. Donnelly et al., Nature Medicine 1, 583 (1995).
12. G. H. Rhodes et al., Dev. Biol. Stand. 82, 229 (1994).
13. H. L. Davis, M. L. Michel, R. G. Whalen, Human Molecular Genetics 2, 1847 (1993).
14. J. B. Ulmer et al., Vaccine 12, 1541 (1994).
15. Z. Xiang and H. C. J. Ertl. Immunity 2, 129 (1995).
16. E. F. Fynan et al, Proc. Natl. Acad. Sci. USA 90, 11478 (1993).
17. E. Manickan, R. J. D. Rouse, Z. Yu, J. Immunol. 155, 259 (1995).
18. M. Sedegah, R. Hedstrom, P. Hobart, S. L. Hoffman, Proc. Natl. Acad. Sci. USA 91, 9866 (1994).
19. M. A. Barry, W. C. Lai, S. A. Johnston, Nature 377, 632 (1995).
20. D. Xu and F. Y. Liew, Vaccine 12, 1534 (1994).
21. D. B. Lowrie, R. E. Tascon, M. J. Colston, Vaccine 12, 1537 (1994).

22. J. W. Moulder, Microbiol. Rev. 55, 143 (1991).
23. J. Schachter, Curr. Top. Microbiol. Immunol. 138, 109 (1988).
24. S. D. Hillis and J. N. Wasserheit, N. Engl. J. Med. 334, 1399 (1996).
25. R. C. Brunham and R. W. Peeling, Infectious Agents and Disease 3, 218 (1994).
26. R. P. Morrison, D. S. Manning, H. D. Caldwell, in Advances in Host Defence Mechanisms, T. C. Quin, Ed. (Raven Press, New York, 1992), pp 57–84.
27. J. T. Grayston and S.-P. Wang, Sex. Trans. Dis. 5, 73 (1978).
28. J. T. Grayston and S.-P. Wang, J. Infect. Dis. 132, 87 (1975).
29. H. R. Taylor, J. Whittum-Hudson, J. Schachter, Invest. Ophthalmol. Vis. Sci. 29, 1847 (1988).
30. B. E. Batteiger, R. G. Rank, P. M. Bavoil, J. Gen. Microbiol. 139, 2965 (1993).
31. M. Campos et al., Invest. Ophthalmol. Vis. Sci. 36, 1477 (1995).
32. H. Su, M. Parnell, H. D. Caldwell, Vaccine 13, 1023 (1995).
33. T.-W. Tan, A. J. Herring, I. E. Anderson, Infect. Immun. 58, 3101 (1990).
34. M. Tuffrey, F. Alexander, W. Conlan, J. Gen. Microbiol. 138, 1707 (1992).
35. Y.-X. Zhang, J. G. Fox, Y. Ho, Mol. Biol. Evol. 10, 1327 (1993).
36. R. P. Morrison, K. Feilzer, D. B. Tumas, Infect. Immun. 63, 4661 (1995).
37. H. Su and H. D. Caldwell, Infect. Immun. 63, 3302 (1995).
38. J. U. Igietseme et al., Reg. Immunol. 5, 317 (1993).
39. J. U. Igietseme and R. G. Rank, Infect. Immun. 59, 1346 (1991).
40. D. M. Williams, J. Schachter, J. J. Coalson, J. Infect. Dis. 149, 630 (1984).
41. G. Tipples and G. McClarty, J. Biol. Chem. 270, 7908 (1995).
42. X. Yang, K. T. HayGlass, R. C. Brunham, J. Immunol., 156, 4338 (1996).
43. Tang et al., Nature 1992, 356: 152–154.
44. Furth et al., Vaccine 1994, 12: 1503–1509.
45. Morrison RP, Manning DS, Caldwell HD. Immunology of *Chlamydia trachomatis* infections: Immunoprotective and immunopathogenetic responses. In: Quin TC. Advances in host defence mechanisms. Sexually transmitted diseases. Vol. 8. New York: Raven Press, 1992: 57–84.

What I claim is:

1. A method of using a nucleic acid encoding a serine-threonine kinase (STK) of a strain of *Chlamydia trachomatis* and having SEQ ID NO: 1 to produce an immune response in a host, which comprises:
   isolating said nucleic acid,
   operatively linking said nucleic acid to a human cytomegalovirus major immediate-early promoter-enhancer region contained within plasmid pcDNA3 to produce a plasmid vector, said cytomegalovirus promoter directing expression of said STK when introduced to a host to produce an immune response to said STK, and
   introducing said vector into a host intramuscularly or intranasally.

2. The method of claim 1 wherein said strain of *Chlamydia* is a strain producing chlamydial infections of the lung.

3. The method of claim 1 wherein said host is a human host.

* * * * *